United States Patent
Kadambi et al.

[11] Patent Number: 5,947,955
[45] Date of Patent: Sep. 7, 1999

[54] ACTIVE EYE MOVEMENT AND POSITIONING CONTROL DEVICE

[75] Inventors: Vivek Kadambi, Indiranagar, India; Fuqian Tang, Orlando, Fla.

[73] Assignee: LaserSight Technologies, Inc., Orlando, Fla.

[21] Appl. No.: 08/928,737

[22] Filed: Sep. 12, 1997

[51] Int. Cl.⁶ .................................................. A61B 17/36
[52] U.S. Cl. ................................ 606/4; 351/205; 351/221
[58] Field of Search ................................ 606/2, 4–6, 13, 606/17, 161, 166; 351/205, 211, 212, 221, 214; 600/27; 607/88

[56] References Cited

U.S. PATENT DOCUMENTS

| | | |
|---|---|---|
| 4,196,980 | 4/1980 | Heine . |
| 4,274,716 | 6/1981 | Gammon . |
| 5,265,598 | 11/1993 | Searfoss et al. .......................... 600/27 |

*Primary Examiner*—Michael Peffley
*Assistant Examiner*—Bryan K. Yarnell
*Attorney, Agent, or Firm*—Farkas & Manelli PLLC; William H. Bollman

[57] ABSTRACT

A device for controlling the position of a patient's eyes during ophthalmic laser surgery is disclosed which comprises a first fixation object positioned within view of the patient's eye that is undergoing treatment, a second fixation object positioned within view of the patient's eye that is not undergoing treatment, and structure for controlling the position of the second fixation object. The present device allows the patient to maintain fixation on a visual target and maintain the eye undergoing treatment in a steady position even when vision in the eye undergoing treatment becomes blurred during laser ablation.

58 Claims, 1 Drawing Sheet

ACTIVE EYE MOVEMENT AND POSITIONING CONTROL DEVICE

BACKGROUND OF THE INVENTION

The present invention relates generally to ophthalmic refractive laser surgery systems and more particularly to a device for actively controlling movement and position of both of the eyes during ophthalmic refractive laser surgery.

Lasers, such as UV (ultraviolet) or IR (infrared), are utilized in ophthalmic surgery to ablate the cornea of the eye in order to correct for abnormal conditions of the eye. Such lasers remove tissue from the cornea to reshape the surface of the cornea for refractive correction or for therapeutic surgery. Conventionally, when using laser devices, there is a fixation object for a patient to fixate an eye undergoing treatment upon during the surgery. Such fixation object typically takes the form of a blinking light source or an image of a light source. The fixation object is co-linear with the path of the laser beam and the line of sight or the visual axis of the eye being treated. In this manner, the eye being treated will remain steady by looking at the fixation object. During surgery the laser beam will be continuously ablating the cornea along the visual axis of the eye being treated.

Although such conventional fixation device has been useful there are several disadvantages associated with its use. One such disadvantage is that the patient undergoing treatment may not have full vision in the eye being treated and will not be able to see the fixation light. In particular, the surface of the cornea of the eye being treated is usually not a smooth surface due to the laser treatment or due to the removal of the flap during an LASIK procedure which prevents the patient from having full vision. Additionally, the patient can completely lose sight of the fixation object. In this case, the patient can become anxious and attempt to search for the fixation object which can cause the eye to move irregularly resulting in a poor outcome of the surgery.

Another disadvantage is that the fixation object is immobile which causes the treated eye to tire easily and to move off center. When this occurs the eye is no longer in fixation and again effective treatment may not result due to the movement of the eye being treated.

When the fixation object is a light source, the light can be reflected by the patient's eye. This reflected light enters the surgeon's eye through optics associated with a viewing microscope. This causes the surgeon to see a bright image of the fixation light on the eye of the patient. The reflected image can distract the surgeon and also impair the judgment of the surgeon during surgery.

Another problem associated with the use of a conventional fixation object is that the laser beam, the fixation light, and the microscope are not exactly co-axial with each other. When not in alignment, the patient's eye is not perpendicular to the laser beam. This may result in the patient's eye not being centered on the fixation object and misalignment of the laser beam.

A further problem may occur in the situation where an eye tracking system, such as an CCD camera, is being used during ophthalmic laser surgery to track movement of the eye undergoing treatment. In this situation, the laser beam is responsive to the eye tracking system to follow the movement of the eye as it shifts off center. The laser beam is adapted to always ablate centrally, however, the laser beam is now no longer collinear with the visual axis of the eye or normal to the surface of the eye. In this situation, the laser beam may ablate the wrong area of the cornea which results in not reshaping the cornea correctly.

The present invention is designed to obviate and overcome many of the disadvantages and shortcomings experienced by using a fixation object or target with the eye undergoing treatment, and to provide a device for actively controlling and positioning the eyes during refractive laser surgery. The present invention is intended to eliminate any unintended movement of the eyes undergoing treatment and to provide a device which assists accurate positioning of the eye prior to and during use of a laser to ablate the surface of the eye. There exist a need to provide an improved device for precisely aligning a laser beam before and during laser surgery while reducing movement of an eye undergoing treatment.

SUMMARY OF THE INVENTION

The present invention is a device for controlling the position of a patient's eyes during ophthalmic laser surgery which comprises a first fixation object positioned within view of the patient's eye that is undergoing treatment, a second fixation object positioned within view of the patient's eye that is not undergoing treatment, and means for controlling the position of the second fixation object.

In another form of the present invention a device for controlling the movement of a patient's eyes during ophthalmic laser surgery is disclosed. The device comprises a first fixation object associated with a patient's eye to be treated, the first fixation object being fixed in position, a second fixation object associated with the other patient's eye that is not being treated, the second fixation object being capable of being movable, and means for controlling the movement of the second fixation object.

According to the present invention, two distinct fixation targets or objects are mounted on or near the laser surgical system in a manner that allows the patient to fixate on one target with the untreated eye and on the other target with the eye undergoing treatment. Vision in the non-operative eye remains unaffected throughout the surgery, and therefore, the non-operative eye is able to maintain fixation and to reduce eye movement. The operative eye will track movement in the non-operative eye with the result that the position of both of the patient's eyes will be controlled during the entire procedure.

In light of the foregoing comments, it will be recognized that a principal object of the present invention is to provide a device that aids the patient in maintaining the eye in proper position during refractive laser surgery even when sight through the eye undergoing treatment becomes blurred or obscured.

Another object of the present invention is to aid proper positioning of the patient's eye by dynamically controlling the movement and position of the eye during ophthalmic surgical procedures.

A further object of the present invention is to provide a device for controlling the position of a patient's eyes during ophthalmic laser surgery which may be employed with highly reliable results and is easy to operate.

These and other objects and advantages of the present invention will become apparent after considering the following detailed specification in conjunction with the accompanying drawings, wherein:

DESCRIPTION OF THE PREFERRED EMBODIMENT

Figure 1:
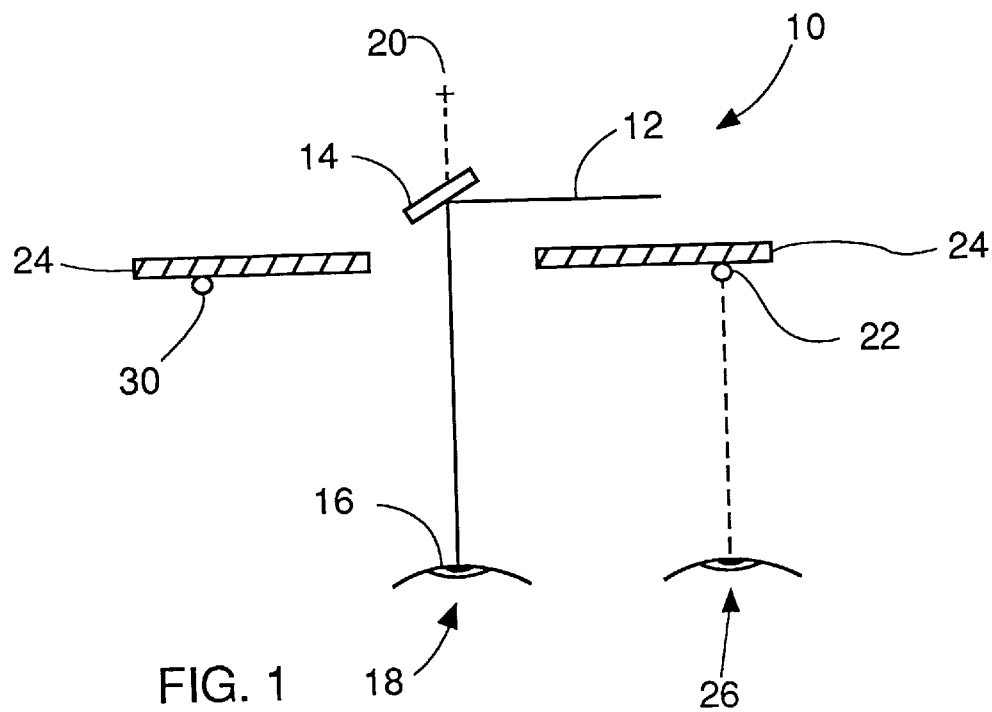
FIG. 1 is a diagrammatic illustration, shown partially in cross-section, of a device for controlling the position of a patient's eyes during ophthalmic laser surgery constructed according to the present invention.

Referring now to the drawings, wherein like numerals refer to like items, number 10 identifies a preferred embodiment of the device of the present invention, which embodiment is most clearly depicted in FIG. 1. With reference now to FIG. 1, the device 10 comprises a laser beam 12 from a laser source (not shown) for delivering ablative laser radiation. The laser beam 12 is reflected by a reflecting mirror 14 onto a cornea 16 of a patient's eye 18. For the purposes of illustration, the patient's eye 18 is the eye which will be undergoing treatment during a surgical procedure. The device 10 further comprises a first fixation target or object 20 associated with the patient's eye 18 with the first fixation object 20 being collinear with the laser beam 12 to center the eye 18 relative to the laser beam 12.

A second fixation target or object 22 is shown attached to a housing 24 of the device 10. The housing 24 holds all of the components of the device 10 which includes the laser source (not shown), the first fixation object 20, the reflecting mirror 14, a microscope (not shown), and various other components, which are also not shown. The second fixation object 22 is associated with an eye 26 which is not undergoing treatment. Examples of the second fixation object 22 are a light source, images of a light, or an image. Additionally, the second fixation object 22 may be movable relative to the housing 24 and the eye 26. Whereas, the first fixation object 20 is stationary. A third fixation object 30 is also shown attached to the housing 24. The third fixation object 30 may be used to fixate the eye 18 when it is not the eye undergoing laser treatment. For example, the housing 24 may be movable relative to the eyes 18 and 26 to position the eye 18 under the third fixation object 30 and then treat the eye 26. The third fixation object 30 may also be movable relative to the housing 24 and the eye 18. Although a third fixation object 30 is shown with reference to FIG. 1, it is also possible to use the second fixation object 22 and either move the patient or the housing 24 to position the second fixation object 22 above the eye 18.

The first fixation object 20 and the second fixation object 22 may be designed to be able to appear and to disappear. For example, if the first and second fixation objects 20 and 22 are light sources, then the objects 20 and 22 may be turned on or off. It is also preferable to have the objects 20 and 22 appear very different. For example, the objects 20 and 22 may be light sources having different colors, shapes, brightness or one of the objects may be a blinking light source while the other object may be a steady light source. It is also desirable to isolate each of the objects 20 and 22 from the other or to make it invisible to the other eye. This may be accomplished by use of an eye cup, tube, shield, or other similar device being placed over the eye or the fixation object such that only one eye can see its associated fixation object. The fixation objects 20 and 22 should also be designed to appear optically at infinity. Lenses, mirrors, or prisms may be used to make the fixation objects 20 and 22 appear as images located very far away and above the respective eyes 18 and 26. The third fixation object 30 may have the same characteristics as discussed above with respect to the second fixation object 22.

Operation of the device 10 is best described as follows. Prior to surgery the patient is instructed to look at the fixation targets 20 and 22 with each respective eye one at a time as the fixation targets 20 and 22 are made to alternately appear and disappear. This process of alternating the fixation targets 20 and 22 breaks the fusion between the two eyes 18 and 26 so that the second fixation target 22 is not visible to the eye 18 being treated during surgery. When the objects 20 and 22 are made very different from each other this facilitates the breakage of the fusion between the eyes 18 and 26. Once fusion between the eyes 18 and 26 is broken, the first fixation target 20 is turned off or otherwise taken from view of the eye 18 and the second fixation target 22 is turned on or otherwise brought into view of the eye 26. The second fixation object 22 may be moved or adjusted to move the eye 18 into a position where the eye 18 appears centered and normal to the view of the microscope. After the eye 18 appears centered it is advantageous to repeat the alternative fixation process again to confirm breakage of fusion between the eyes 18 and 26.

Surgery may now take place and during surgery the second fixation object 22 is typically visible. The first fixation object 20 is removed or made to disappear moments before surgery is begun and such removal should occur throughout the surgery. Removal of the first fixation target 20 helps to eliminate movement of the eye 18 searching for the first fixation target 20 during surgery. As discussed above, the vision of eye 18 may become blurred during surgery and the target 20 may not be visible to the eye 18. Another advantage associated with removal of the target 20 is that there is no light reflected back into the surgeon's eyes to distract the surgeon or impair the surgeon's judgment.

While the untreated eye 26 is focused on the second fixation object 22, the treated eye 18 will be centered and normal to the laser beam 12 due to the breakage of fusion and the centration process prior to surgery. Since the untreated eye 26 has good vision throughout surgery, the patient will be able to fixate much easier. In this event, the eye 18 being treated will be more steady and this will result in better clinical results. Additionally, the surgeon may be able to adjust the position of the second fixation object 22 during surgery which allows the surgeon to move or reposition the treated eye 18. This allows the surgeon to rely on the surgeon's judgment instead of totally depending upon the alignment capabilities of the housing 24.

It is also possible and contemplated to be able to control eye movement and positioning dynamically by oscillating the second fixation object 22 about a central reference position within a small range of movement during surgery. This provides for less tiring of the eye 26 because it is looking at a moving target or object 22. Although it may cause the eye 18 to move off center during surgery, this amount of offset is minimal and should be acceptable for purposes of surgery. For example, as a rough estimate, if the distance between the eye 26 and the second fixation object 22 is about 5 inches or 127 mm and if it is assumed that the eye rotates about the center of the eye ball 15 mm below the surface of the cornea, then the offset amount is only about 0.1 mm for a 1 mm range of oscillation of the second fixation object 22. If the second fixation object 22 oscillates within a 1 mm range quickly and randomly, the eye 18 will also move quickly in the 0.1 mm range. This will also create a desirable polishing effect.

Figure 2:
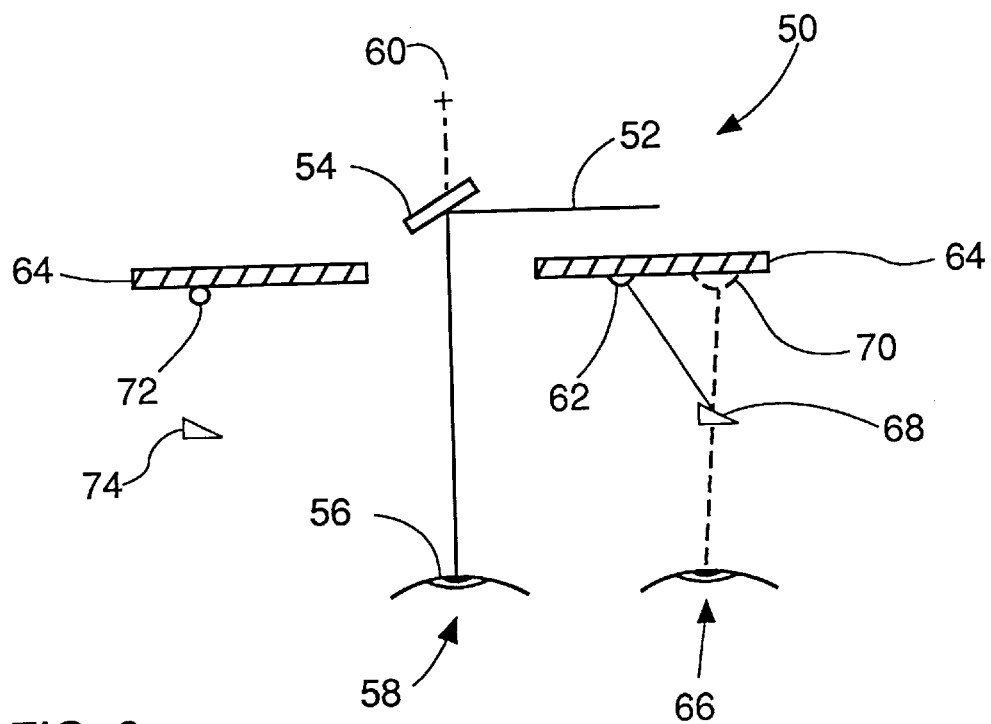
FIG. 2 is a diagrammatic illustration, shown partially in cross-section, of a second preferred embodiment of a device for controlling the position of a patient's eyes during ophthalmic laser surgery constructed according to the present invention.

Referring now to FIG. 2, a second preferred embodiment of a device 50 comprises a laser beam 52 from a laser source (not shown) for delivering ablative laser radiation. The laser beam 52 is reflected by a reflecting mirror 54 onto a cornea 56 of a patient's eye 58. The device 50 further comprises a first fixation target or object 60 associated with the patient's eye 58 with the first fixation object 60 being collinear with the laser beam 52 to center the eye 58 relative to the laser beam 52.

A second fixation target or object 62 is shown attached to a housing 64 of the device 50. The housing 64 holds all of the components of the device 50 which includes the laser source (not shown), the first fixation object 60, the reflecting mirror 54, a microscope (not shown), and various other components, which are also not shown. The second fixation object 62 is associated with an eye 66 which is not undergoing treatment. Examples of the second fixation object 62 are a light source, images of a light, or an image. Additionally, the second fixation object 62 may be movable relative to the housing 64 and the eye 66. Whereas, the first fixation object 60 is stationary. Also associated with the second fixation object 62 is a movable prism 68 which is adapted to be moved instead of moving the second fixation object 62. For example, the prism 68 may only have to be manipulated in translational, rotational, or tilting movement to move the eye 66. The prism 68 is capable of providing an optical image 70 of the second fixation object 62 to the eye 66. In this manner, the location of the optical image 70 may be changed or adjusted without having to move the second fixation object 62.

A third fixation object 72 is also shown attached to the housing 64 and also including an associated movable prism 74. The third fixation object 72 may be used to fixate the eye 58 when it is not the eye undergoing laser treatment. For example, the housing 64 may be movable relative to the eyes 58 and 66 to position the eye 58 under the third fixation object 72 and then treat the eye 66. The prism 74 is movable relative to the third fixation object 72 and the eye 58. Although a third fixation object 72 and its respective prism 74 are shown with reference to FIG. 2, it is also possible to use the second fixation object 62 and either move the patient or the housing 64 to position the second fixation object 62 and the prism 68 above the eye 58.

The first fixation object 60 and the second fixation object 62 may be designed to be able to appear and to disappear. For example, if the first and second fixation objects 60 and 62 are light sources, then the objects 60 and 62 may be turned on or off. It is also preferable to have the objects 60 and 62 appear very different. For example, the objects 60 and 62 may be light sources having different colors, shapes, brightness or one of the objects may be a blinking light source while the other object may be a steady light source. It is also desirable to isolate each of the objects 60 and 62 from the other or to make it invisible to the other eye. This may be accomplished by use of an eye cup, tube, shield, or other similar device being placed over the eye or the fixation object such that only one eye can see its associated fixation object. The fixation objects 60 and 62 should also be designed to appear optically at infinity. Lenses, mirrors, or prisms may be used to make the fixation objects 60 and 62 appear as images located very far away and above the respective eyes 58 and 66. The third fixation object 72 may have the same characteristics as discussed above with respect to the second fixation object 62.

Operation of the device 50 is similar to operation of the device 10 which was previously discussed. In particular, prior to surgery the patient is instructed to look at the fixation targets 60 and 62 with each respective eye one at a time as the fixation targets 60 and 62 are made to alternately appear and disappear. This process of alternating the fixation targets 60 and 62 breaks the fusion between the two eyes 58 and 66 so that the second fixation target 62 is not visible to the eye 58 being treated during surgery. Making the objects 60 and 62 different from each other also facilitates the breakage of the fusion between the eyes 58 and 66. Once fusion between the eyes 58 and 66 is broken, the first fixation target 60 is turned off or otherwise taken from view of the eye 58 and the second fixation target 62 is turned on or otherwise brought into view of the eye 66. The second fixation object 62 may be moved by use of the prism 68 to facilitate movement of the eye 58 into a position where the eye 58 appears centered and normal to the view of the microscope. After the eye 58 appears centered it is advantageous to repeat the alternative fixation process again to confirm breakage of fusion between the eyes 58 and 66.

Surgery may now take place and during surgery the second fixation object 62 is typically visible. The first fixation object 60 is removed or made to disappear moments before surgery is begun and such removal should occur throughout the surgery. Removal of the first fixation target 60 helps to eliminate movement of the eye 58 searching for the first fixation target 60 during surgery. As discussed above, the vision of eye 58 may become blurred during surgery and the target 60 may not be visible to the eye 58. Another advantage associated with removal of the target 60 is that there is no light reflected back into the surgeon's eyes to distract the surgeon or impair the surgeon's judgment.

While the untreated eye 66 is focused on the second fixation object 62, the treated eye 58 will be centered and normal to the laser beam 52 due to the breakage of fusion and the centration process prior to surgery. Since the untreated eye 66 has good vision throughout surgery, the patient will be able to fixate much easier. In this event, the eye 58 being treated will be more steady and this will result in better clinical results. Additionally, the surgeon may be able to adjust the position of the second fixation object 62 during surgery by movement of the prism 68 which allows the surgeon to move or reposition the treated eye 58. Movement of the prism 68 may be manual or automated.

The devices 10 or 50 may also be combined with a topographic device, such as a topographic camera, to monitor the treated eye. The topographic device may be used to check the centration and angular alignment of the cornea with the laser beam.

The devices 10 or 50 are also useful in eccentric situations where the area of the eye to be treated is not centered on the cornea, such as in the cases of presbiopia or therapeutic surgery. In such eccentric situations the area of the cornea to be ablated is not the central area of the cornea it is some off centered area. It is desirable to align the laser beam with the off centered area to be ablated. The preferred eccentric alignment can be achieved by having the patient look at a fixation object which is off center. With the present invention, such as devices 10 or 50, the surgeon only has to move either the second fixation object 22 or the prism 68 off the central reference position until the treated eye appears in the required eccentric alignment position.

From all that has been said, it will be clear that there has thus been shown and described herein a device for actively controlling eye movement and positioning which fulfills the various objects and advantages sought therefor. It will be apparent to those skilled in the art, however, that many changes, modifications, variations, and other uses and applications of the subject device for actively controlling eye movement and positioning are possible and contemplated. All changes, modifications, variations, and other uses and applications which do not depart from the spirit and scope of the invention are deemed to be covered by the invention, which is limited only by the claims which follow.

What is claimed is:

1. A device for controlling a position of a patient's eyes during ophthalmic surgery, comprising:
   a first fixation object positioned within view of said patient's eye that is undergoing treatment;
   a second fixation object positioned within view of said patient's eye that is not undergoing treatment; and
   means for controlling a position of said second fixation object with respect to said patient's eye that is not undergoing treatment to actively control movement of said patient's eye that is undergoing treatment during said ophthalmic surgery.

2. The device for controlling said position of said patient's eyes during ophthalmic surgery in accordance with claim 1, further comprising:
   means for removing said first fixation object and said second fixation object from view of a respective eye.

3. The device for controlling said position of said eye of said patient during ophthalmic surgery in accordance with claim 1, further comprising:
   a third fixation object adapted to be positioned within view of a patient's eye that has undergone treatment; and
   means for controlling a position of said third fixation object.

4. The device for controlling said position of said eye of said patient during ophthalmic surgery in accordance with claim 3, wherein:
   said first fixation object is fixed in position; and
   said third fixation object is capable of being moved.

5. The device for controlling said position of said patient's eyes during ophthalmic surgery in accordance with claim 1, wherein:
   said first fixation object is fixed in position; and
   said second fixation object is capable of being moved.

6. A device for controlling a position of an eye of a patient during ophthalmic surgery, comprising:
   a first light source positioned within view of said patient's eye that is undergoing treatment;
   a second light source positioned within view of said patient's eye that is not undergoing treatment; and
   means for controlling a position of said second light source.

7. The device for controlling said position of said eye of said patient during ophthalmic surgery in accordance with claim 6, wherein:
   said first light source has a different color than said second light source.

8. The device for controlling said position of said eye of said patient during ophthalmic surgery in accordance with claim 6, wherein:
   said first light source has a different shape than said second light source.

9. The device for controlling said position of said eye of said patient during ophthalmic surgery in accordance with claim 6, wherein:
   said first light source has a different brightness than said second light source.

10. The device for controlling said position of said eye of said patient during ophthalmic surgery in accordance with claim 6, wherein:
    said first light source and said second light source are capable of being turned on and turned off with respect to each other.

11. The device for controlling said position of said eye of said patient during ophthalmic surgery in accordance with claim 6, wherein:
    said first light source is a steady light source; and
    said second light source is a blinking light source.

12. The device for controlling said position of said eye of said patient during ophthalmic surgery in accordance with claim 6, wherein:
    said first light source is a blinking light source; and
    said second light source is source a steady light source.

13. A device for controlling a position of an eye of a patient during ophthalmic surgery, comprising:
    a first fixation object positioned within view of said patient's eye that is undergoing treatment;
    a second fixation object positioned within view of said patient's eye that is not undergoing treatment; and
    a prism adapted to control a position of said second fixation object.

14. The device for controlling said position of said eye of said patient during ophthalmic surgery in accordance with claim 13, wherein:
    said prism is movable to reposition said second fixation object relative to said eye not undergoing treatment.

15. A device for controlling a position of an eye of a patient during ophthalmic surgery, comprising:
    a first light source positioned within view of said patient's eye that is undergoing treatment;
    a second light source positioned within view of said patient's eye that is not undergoing treatment;
    means for controlling a position of said second light source;
    a third light source adapted to be positioned within view of said patient's eye that has undergone treatment; and
    means for controlling a position of said third light source.

16. The device for controlling said position of said eye of said patient during ophthalmic surgery in accordance with claim 15, wherein:
    said first light source has a different color than said third light source.

17. The device for controlling said position of said eye of said patient during ophthalmic surgery in accordance with claim 15, wherein:
    said first light source has a different shape than said third light source.

18. The device for controlling said position of said eye of said patient during ophthalmic surgery in accordance with claim 15, wherein:
    said first light source has a different brightness than said third light source.

19. The device for controlling said position of said eye of said patient during ophthalmic surgery in accordance with claim 15, wherein:
    said first light source and said third light source are capable of being turned on and turned off with respect to each other.

20. The device for controlling said position of said eye of said patient during ophthalmic surgery in accordance with claim 15, wherein:
    said first light source is a steady light source; and
    said third light source is a blinking light source.

21. The device for controlling said position of said eye of said patient during ophthalmic surgery in accordance with claim 15, wherein:
    said first light source is a blinking light source; and said third light source is a steady light source.

22. A device for controlling a position of an eye of a patient during ophthalmic surgery, comprising:

a first fixation object positioned within view of said patient's eye that is undergoing treatment;

a second fixation object positioned within view of said patient's eye that is not undergoing treatment;

means for controlling a position of said second fixation object;

a third fixation object adapted to be positioned within view of said patient's eye that has undergone treatment: and a prism adapted to control a position of said third fixation object.

23. The device for controlling said position of said eye of said patient during ophthalmic surgery in accordance with claim 22, wherein:

said prism is movable to reposition said third fixation object relative to said eye that has undergone treatment.

24. A device for controlling a position of a patient's eyes during ophthalmic laser surgery, comprising:

a first light source associated with a patient's eye to be treated, said first light source being fixed in position;

a second light source capable of being moved; and means for controlling movement of said second light source.

25. The device for controlling said position of said patient's eyes during ophthalmic laser surgery in accordance with claim 24, further comprising:

a third light source associated with a patient's eye which has been treated, said third light source being capable of being moved; and means for controlling movement of said third light source.

26. A device for controlling movement of an eye of a patient during ophthalmic surgery, comprising:

at least one movable fixation object positioned to be visible to an eye not being treated and not visible to an eye being treated, said at least one movable fixation object being moved to actively control movement of said eye being treated during said ophthalmic surgery.

27. The device for controlling movement of said eye of said patient during ophthalmic surgery in accordance with claim 26, further comprising:

a stationary fixation object visible to said eye being treated.

28. The device for controlling movement of said eye of said patient during ophthalmic surgery in accordance with claim 27, wherein:

said stationary fixation object is removed from view of said eye being treated.

29. The device for controlling movement of said eye of said patient during ophthalmic surgery in accordance with claim 27, wherein:

an appearance of said stationary fixation object is different than an appearance of said at least one movable fixation object.

30. The device for controlling movement of said eye of said patient during ophthalmic surgery in accordance with claim 27, wherein:

said stationary fixation object and said at least one movable fixation object are made to appear and disappear alternatively with respect to each other.

31. The device for controlling movement of said eye of said patient during ophthalmic surgery in accordance with claim 27, wherein:

said stationary fixation object and said at least one movable fixation object are each a light source.

32. The device for controlling movement of said eye of said patient during ophthalmic surgery in accordance with claim 31, wherein:

said stationary fixation object and said at least one movable fixation object are capable of being turned on and turned off alternatively with respect to each other.

33. The device for controlling movement of said eye of said patient during ophthalmic surgery in accordance with claim 31, wherein:

said stationary fixation object is a blinking light source; and said at least one movable fixation object is a steady light source.

34. The device for controlling movement of said eye of said patient during ophthalmic surgery in accordance with claim 31, wherein:

said stationary fixation object is a steady light source; and said at least one movable fixation object is a blinking light source.

35. The device for controlling movement of said eye of said patient during ophthalmic surgery in accordance with claim 26, wherein:

a prism is used to move said at least one movable fixation object with respect to said eye not being treated.

36. The device for controlling movement of said eye of said patient during ophthalmic surgery in accordance with claim 26, wherein:

said at least one movable fixation object is oscillated about a center reference point.

37. A method of controlling movement of an eye of a patient during ophthalmic surgery, comprising:

providing at least one movable fixation object in a position visible to an eye not being treated and not visible to an eye being treated; and controlling a position of said at least one movable fixation object to actively control movement of said eye being treated during said ophthalmic surgery.

38. The method of controlling movement of said eye of said patient during ophthalmic surgery in accordance with claim 37, further comprising:

providing a stationary fixation object visible to said eye being treated.

39. The method of controlling movement of said eye of said patient during ophthalmic surgery in accordance with claim 38, further comprising:

removing said stationary fixation object from view of said eye being treated.

40. The method of controlling movement of said eye of said patient during ophthalmic surgery in accordance with claim 38, wherein:

making an appearance of said stationary fixation object to be different than an appearance of said at least one movable fixation object.

41. The method of controlling movement of said eye of said patient during ophthalmic surgery in accordance with claim 38, further comprising:

making said stationary fixation object appear to said eye being treated when said at least one movable fixation object is made to disappear from view of said eye not being treated.

42. The method of controlling movement of said eye of said patient during ophthalmic surgery in accordance with claim 38, further comprising:

making said stationary fixation object disappear from view of said eye being treated when said at least one movable fixation object is made to appear to said eye not being treated.

43. The method of controlling movement of said eye of said patient during ophthalmic surgery in accordance with claim 37, further comprising:

oscillating said at least one movable fixation object about a center reference point.

44. A device for controlling a position of a patient's eyes during ophthalmic surgery, comprising:

a first fixation object positioned within view of said patient's eye that is undergoing treatment; and a second fixation object positioned within view of said patient's eye that is not undergoing treatment;

wherein position of said second fixation object is controlled with respect to said patient's eye that is not undergoing treatment to actively control movement of said patient's eye that is undergoing treatment during said ophthalmic surgery.

45. The device for controlling said position of said eye of said patient during ophthalmic surgery in accordance with claim 44, further comprising:

a third fixation object adapted to be positioned within view of a patient's eye that has undergone treatment.

46. The device for controlling said position of said patient's eyes during ophthalmic surgery in accordance with claim 44, wherein:

said first fixation object is removed from view of said patient's eye that is undergoing treatment.

47. A device for controlling a position of an eye of a patient during ophthalmic surgery, comprising:

a first light source positioned within view of said patient's eye that is undergoing treatment;

a second light source positioned within view of said patient's eye that is not undergoing treatment; and a controller adapted to control position of said second light source.

48. The device for controlling said position of said eye of said patient during ophthalmic surgery in accordance with claim 47, wherein:

said first light source has a different color than said second light source.

49. The device for controlling said position of said eye of said patient during ophthalmic surgery in accordance with claim 47, wherein:

said first light source has a different shape than said second light source.

50. The device for controlling said position of said eye of said patient during ophthalmic surgery in accordance with claim 47, wherein:

said first light source has a different brightness than said second light source.

51. The device for controlling said position of said eye of said patient during ophthalmic surgery in accordance with claim 47, wherein:

said first light source and said second light source are capable of being turned on and turned off with respect to each other.

52. A device for controlling a position of an eye of a patient during ophthalmic surgery, comprising:

a first fixed light source positioned within view of said patient's eye that is undergoing treatment;

a second light source positioned within view of said patient's eye that is not undergoing treatment;

a first controller adapted to control a position of said second light source;

a third light source adapted to be positioned within view of said patient's eye that has undergone treatment; and a second controller adapted to control a position of said third light source.

53. The device for controlling said position of said eye of said patient during ophthalmic surgery in accordance with claim 52, wherein:

said first light source has a different color than said third light source.

54. The device for controlling said position of said eye of said patient during ophthalmic surgery in accordance with claim 52, wherein:

said first light source has a different shape than said third light source.

55. The device for controlling said position of said eye of said patient during ophthalmic surgery in accordance with claim 52, wherein:

said first light source has a different brightness than said third light source.

56. The device for controlling said position of said eye of said patient during ophthalmic surgery in accordance with claim 52, wherein:

said first light source and said third light source are capable of being turned on and turned off with respect to each other.

57. A device for controlling a position of a patient's eyes during ophthalmic laser surgery, comprising:

a first light source associated with a patient's eye to be treated, said first light source being fixed in position;

a second light source capable of being moved; and a first controller adapted to control movement of said second fixation object.

58. The device for controlling said position of said patient's eyes during ophthalmic laser surgery in accordance with claim 57, further comprising:

a third light source associated with a patient's eye which has been treated, said third light source being capable of being moved; and a second controller adapted to control movement of said third light source.

* * * * *